(12) United States Patent
Ruben et al.

(10) Patent No.: US 8,131,394 B2
(45) Date of Patent: *Mar. 6, 2012

(54) METHOD OF AND SYSTEM FOR LABELING CONTAINERS OF PRESCRIBED MEDICINE

(75) Inventors: Dennis Ruben, Lincolnwood, IL (US); Allen Yeung, Addison, IL (US)

(73) Assignee: Rxperts, Inc., Morton, IL (US)

( * ) Notice: Subject to any disclaimer, the term of this patent is extended or adjusted under 35 U.S.C. 154(b) by 611 days.

This patent is subject to a terminal disclaimer.

(21) Appl. No.: 11/835,638

(22) Filed: Aug. 8, 2007

(65) Prior Publication Data

US 2008/0046287 A1 Feb. 21, 2008

Related U.S. Application Data

(63) Continuation of application No. 11/384,819, filed on Mar. 21, 2006, now Pat. No. 7,257,456, which is a continuation of application No. 09/466,282, filed on Dec. 17, 1999, now Pat. No. 7,016,752.

(51) Int. Cl.
*G06F 19/00* (2006.01)

(52) U.S. Cl. ............ 700/117; 700/231; 283/70; 283/81; 283/900

(58) Field of Classification Search .................. 700/117, 700/231, 235, 237, 90; 283/70, 75, 81, 67, 283/900; 206/534, 538; 705/2, 3
See application file for complete search history.

(56) References Cited

U.S. PATENT DOCUMENTS

| | | | |
|---|---|---|---|
| 4,730,849 A | 3/1988 | Siegel | 283/70 |
| 4,732,411 A | 3/1988 | Siegel | 283/75 |
| 4,918,604 A | 4/1990 | Baum | 221/5 |
| 5,174,451 A | 12/1992 | Niven | 206/534 |
| 5,390,796 A | 2/1995 | Kerfoot, Jr. | 206/534 |
| 5,642,906 A | 7/1997 | Foote et al. | 283/67 |
| 5,842,976 A | 12/1998 | Williamson | 600/300 |
| 5,905,652 A | 5/1999 | Kutsuma | 700/235 |
| 7,016,752 B1 * | 3/2006 | Ruben et al. | 700/117 |
| 7,257,456 B2 * | 8/2007 | Ruben et al. | 700/117 |

FOREIGN PATENT DOCUMENTS

WO WO99/17218 4/1999

* cited by examiner

*Primary Examiner* — Albert Decady
*Assistant Examiner* — Steven Garland
(74) *Attorney, Agent, or Firm* — Winston & Strawn LLP

(57) ABSTRACT

A method of and system for labeling containers of prescribed medicine is provided wherein a photograph of a patient is taken using a camera. The photograph is then stored on a computer as a computer software object. When a prescription is filled for the patient, the photograph is printed on the label along with prescription information and the label is attached to the container.

20 Claims, 4 Drawing Sheets

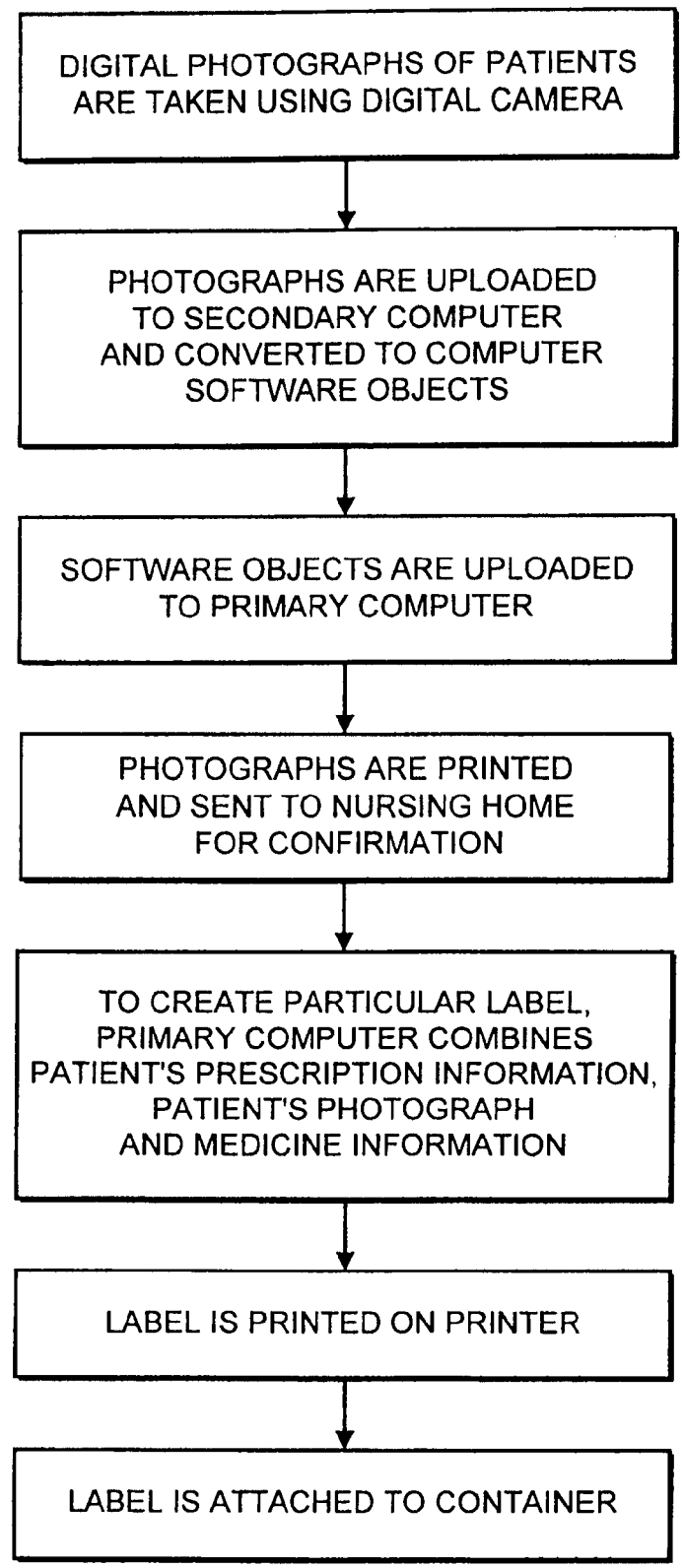
F I G. 2

METHOD OF AND SYSTEM FOR LABELING CONTAINERS OF PRESCRIBED MEDICINE

CROSS REFERENCE TO RELATED APPLICATION

This application is a continuation of U.S. patent application Ser. No. 11/384,819 filed Mar. 21, 2006, which issued as U.S. Pat. No. 7,257,456 on Aug. 14, 2007, which is a continuation of U.S. patent application Ser. No. 09/466,282 filed Dec. 17, 1999, now U.S. Pat. No. 7,016,752, and claims the benefit of both parent applications, each of which are hereby incorporated by reference herein in their entirety.

BACKGROUND OF THE INVENTION

1. Field of the Invention

The present invention relates to prescription medicine. More particularly, the present invention relates to a method of and system for labeling containers of prescribed medicine.

2. Description of the Prior Art

Those of ordinary skill in the art and laypersons alike are well aware of labels which are found on containers of prescribed medicine. Typically, a label on a container of prescribed medicine will contain information such as the name of the patient; the name of the medicine and the dosage particulars; the name of the prescribing doctor; the quantity of medicine in the container; the expiration date of the medicine; a code which identifies the medicine manufacturer; a prescription number; the prescription date; the name and address of the pharmacy which filled the prescription; and a UPC code which can be used by the pharmacy to automatically identify the prescription in its computer system.

Despite the specific patient identifying information found on containers of prescribed medicine, when distributing medicine to a large number of patients, such as in hospitals and nursing homes, patients often receive the wrong medicine. To combat this serious problem, some hospitals and nursing homes take photographs of their patients and include the photographs in the medication administration record (MAR) used to record the administration of medicine. In this way the nurses administering the medicine are provided with means to help ensure that a patient does not receive the wrong medication. These photographs are also sometimes attached to the medication cart itself, such as on a drawer, or on the divider cards used to segregate the patients' medicine. These methods, however, are laborious, time consuming, highly inefficient and potentially dangerous.

SUMMARY OF THE PRESENT INVENTION

Accordingly, it is an object of the present invention to provide a method of and system for labeling containers of prescribed medicine which overcomes the problems associated with the prior art. It is a further object of the present invention to provide a method of and system for labeling containers of prescribed medicine wherein the label includes a photograph of the patient.

The foregoing and other objects are achieved by providing a method of and system for labeling containers of prescribed medicine wherein a photograph of a patient is taken. The photograph is then stored on a computer as a computer software object. When a prescription is filled for the patient, the photograph is printed on the label along with the patient's prescription information and the label is attached to the container.

The present invention will now be described in greater detail, with frequent reference being made to the drawings identified below.

BRIEF DESCRIPTION OF THE DRAWINGS

In the accompanying drawings:

FIG. 2 is a flow chart which illustrates the operation of the labeling system of FIG. 1;

DETAILED DESCRIPTION OF THE PREFERRED EMBODIMENT

The following description is presented to enable any person of ordinary skill in the art to make and use the present invention. Various modifications to the preferred embodiment will be readily apparent to those of ordinary skill in the art, and the principles defined herein may be applied to other embodiments and applications without departing from the spirit and scope of the present invention. Thus, the present invention is not intended to be limited to the embodiment shown, but is to be accorded the broadest scope consistent with the principles and features disclosed herein.

The present invention is designed specifically for use by pharmacies which distribute prescriptions to patients in nursing homes, hospitals, or other large medical institutions. However, it will be realized by those of ordinary skill in the art that the present invention may be used by any pharmacy in distributing prescribed medicine. Thus, the present invention is in no way limited to use in nursing homes and hospitals.

Figure 1:
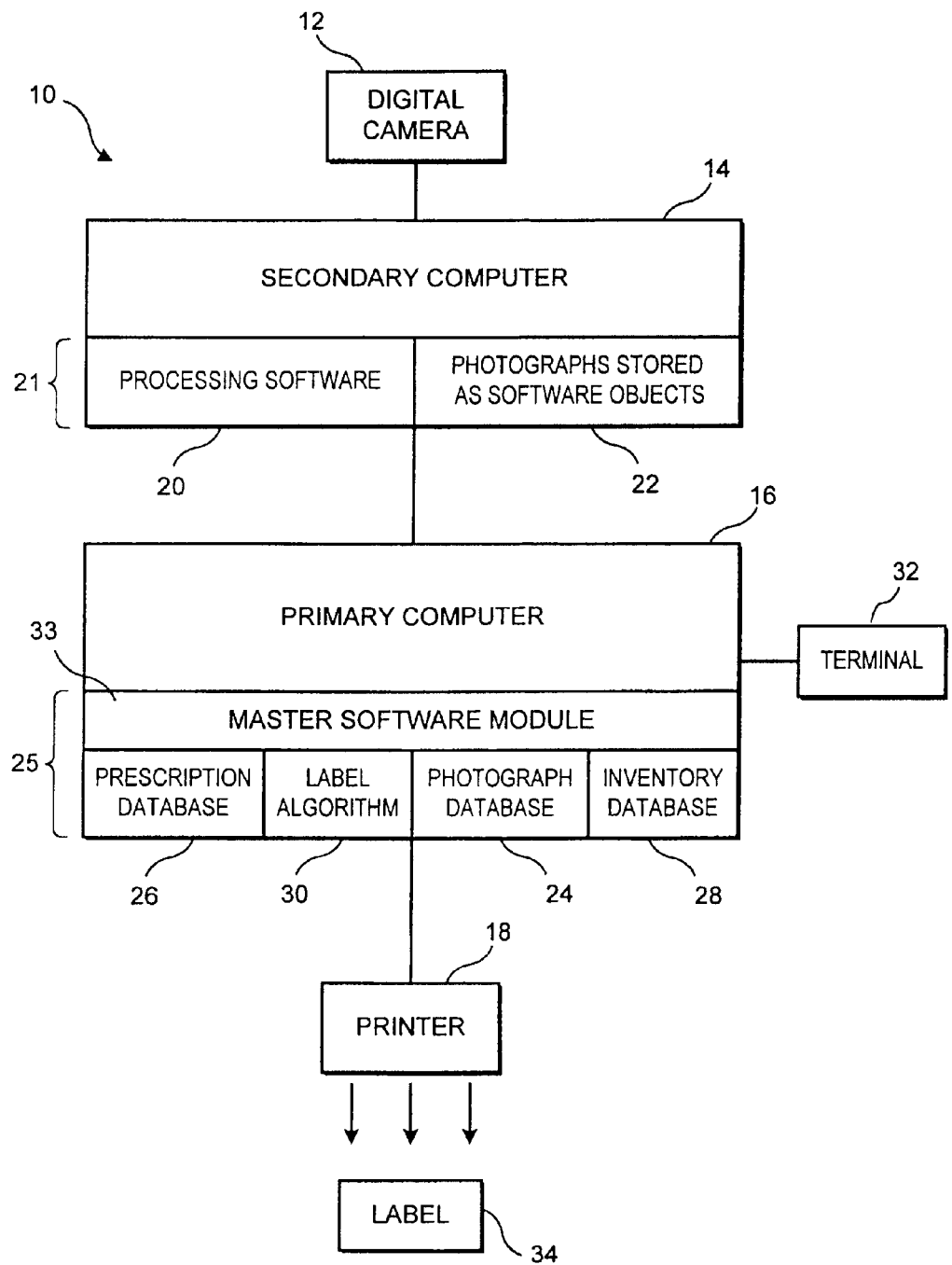
FIG. 1 is a schematic diagram of a labeling system in accordance with the present invention.

Referring to FIG. 1, the system 10 in accordance with the present invention includes a digital camera 12 for taking digital photographs of the patients, such as a Kodak™ digital camera; a secondary computer 14, such as an IBM compatible personal computer, for downloading the digital photographs from the digital camera 12 and converting the photographs into software objects; a primary computer 16, such as a midrange computer, for creating the labels; and a printer 18 attached to the secondary computer 16 for printing the labels.

For purposes of this discussion, it will be assumed that the system 10 will be used by a pharmacy to distribute medicine to patients in a nursing home.

Referring to FIG. 2, using the digital camera 12, a pharmacist, or an agent or employee of the pharmacist, first takes a digital photograph of each nursing home patient. The digital camera 12 is then attached, via an appropriately configured port, to the secondary computer 14 which contains processing software 20 stored in a memory 21 for converting the digital photographs into software objects 22, such as JPEG files. The photographs are then uploaded to the secondary computer 14 from the digital camera 12 and converted into software objects 22. Digital cameras are generally sold with processing software which will run under popular operating systems, such as Windows 95™, which do this conversion. Depending on the number of patients and the capacity of the digital camera 12, this process may need to be repeated a number of times. Additionally, as new patients enter the nursing home, their photographs must be taken as well.

After conversion, the software objects 22 are temporarily stored on the secondary computer 14 in memory 21. It will be realized by those of ordinary skill in the art that the secondary computer 14 may be any type of computer which is capable of performing the functions described herein. However, the secondary computer 14 will typically be an inexpensive IBM™ compatible personal computer having a central-processing-unit (CPU), a hard drive for storing the processing software and the software objects, a random-access-memory (RAM), a read only memory (ROM), a monitor, a keyboard and a mouse, all running under Windows 95™ or the like.

The software objects are next uploaded from the secondary computer 14 to the primary computer 16 via appropriately configured ports on each computer, where they are indexed and stored in a photograph database 24 which is stored in a memory 25. The primary computer 16 also includes stored in memory 25 a prescription database 26 which contains the prescription information of each patient, including the name of the patient, the name of the medicine and the dosage particulars, the name of the prescribing doctor, the name of the nursing home and the quantity of medicine in the prescription, and an inventory database 28 which contains information relating to the medicine which the pharmacist has in stock, including the identity of the manufacturers and the expiration date of the various medicines. The prescription database 26 and the inventory database 28 will be periodically updated as the prescription information of the patients change and as the pharmacist's inventory changes. The primary computer 16 also includes a label algorithm 30 which will create the labels.

While the primary computer may also be an IBM™ compatible computer, it will generally be a more business oriented computer, such as an IBM AS/400™, having a more powerful CPU, more RAM, more ROM, and a hard drive having sufficient memory to hold the various databases described herein. It will be apparent to those of ordinary skill in the art, however, that the primary computer 16 may be any type of computer capable of performing the functions described herein.

Before any prescriptions are filled, the photographs should be confirmed by sending a grid sheet having the name and photograph of every patient to the nursing home, who will ensure that the names and photographs are correctly matched. In this way any errors which may have occurred during the photographing process can be corrected.

When it comes time to fill a prescription for a patient, a pharmacist or a pharmacist's technician or the like will run the label algorithm 30 using a terminal 32 connected to the primary computer 16. Typically, the label algorithm 30 will be launched through a master software module 33 which is used to control the overall operation of the primary computer 15 16, including updating of the various databases. Such master software modules are commercially available and are well known to those of ordinary skill in the art.

Figure 3:
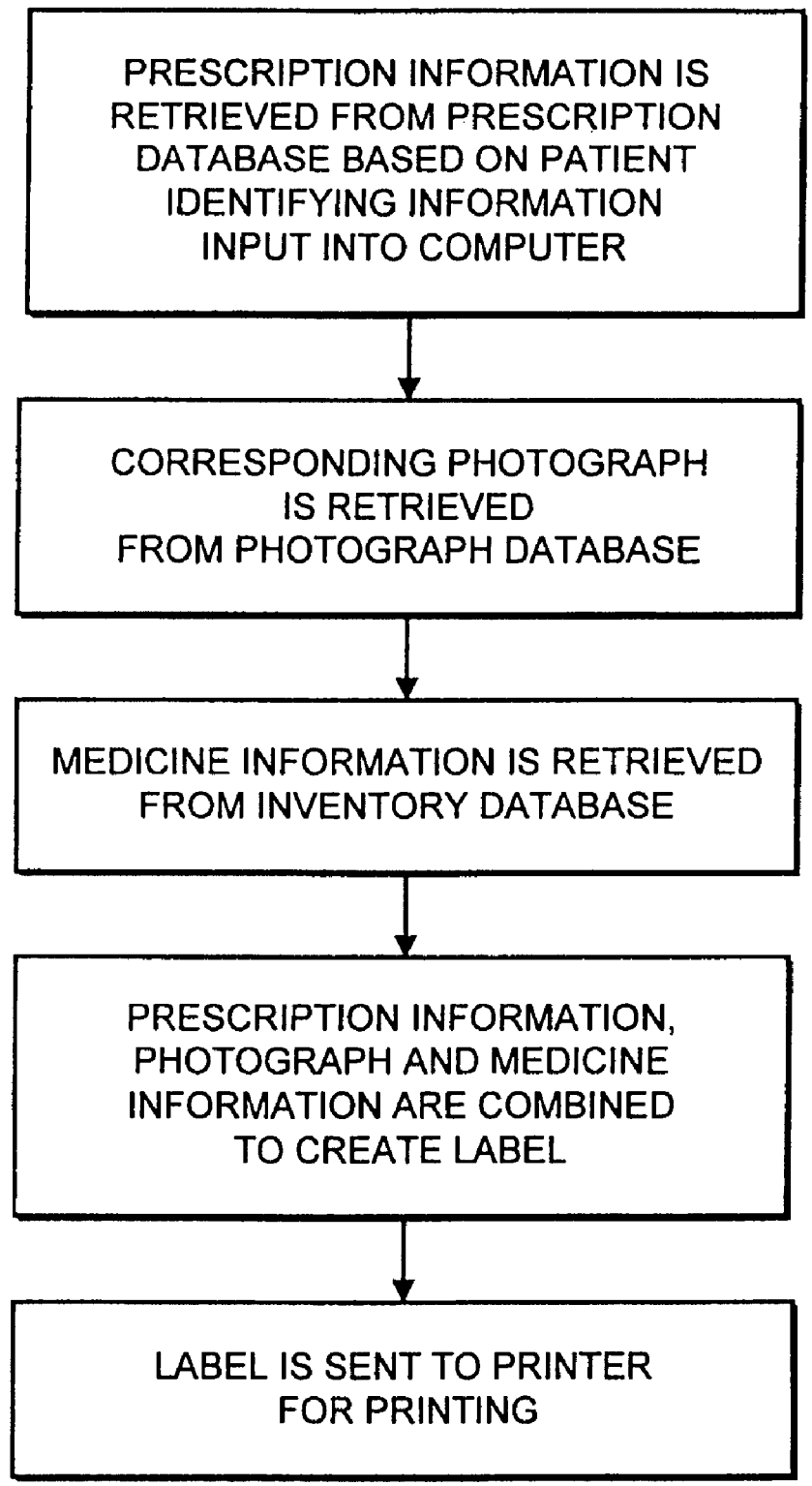
FIG. 3 is a flow chart which illustrates the operation of the label algorithm.

Referring to FIG. 3, which illustrates how the label algorithm functions, the pharmacist or pharmacist's technician or the like will enter information which identifies the patient, such as the patient's name or a prescription number. The label algorithm 30 will then 20 retrieve the prescription information from the prescription database 26, the corresponding photograph from the photograph database 24 and the medicine information from the inventory database 28 and combine the data to create a label. The label will then be printed on the printer 18, which is preferably a laser printer for clarity, but which may be any type of printer. The printed label is then attached to the medicine container, preferably through an adhesive on the back of the label. It will be appreciated that a label algorithm in accordance with the present invention may be readily implemented by one of ordinary skill in the art.

Figure 4:
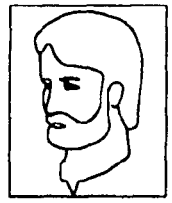
FIG. 4 is a sample label in accordance with the present invention.

A sample label 34 in accordance with the present invention is shown in FIG. 4. As is clear from FIG. 4, the label contains a photograph of the patient, as well as the patient's prescription information. Additionally, the label contains the expiration date of the medicine; a code which identifies the medicine manufacturer; the name and address of the pharmacy which filled the prescription; and a UPC code generated by the label algorithm 30 which can be used by the pharmacy to automatically identify and track the prescription.

It will be realized by those of ordinary skill in the art that the functions performed by the primary and secondary computers may in fact be performed on one computer instead of two, and thus the present invention is not limited to two separate computers. It will also be realized by those of ordinary skill in the art that the present invention is also not limited to use of a digital camera. For example, photographs may be taken using an ordinary camera. After developing, the photographs may be converted to computer software objects using a scanner or the like.

Nor, as discussed above, is the present invention limited to use in nursing homes, hospitals and the like. Rather, it will be apparent to those of ordinary skill in the art that the present invention may be used in any type of pharmacy, including a consumer's neighborhood pharmacy. For example, when a consumer goes to his neighborhood pharmacy to fill a prescription for the first time, the pharmacist can take his/her photograph and store the photograph in the pharmacist's computer. Each time the consumer fills a prescription, his/her photograph will be printed on the label.

Thus, in accordance with the foregoing the objects of the present invention are achieved. Modifications to the above would be obvious to those of ordinary skill in the art, but would not bring the invention so modified beyond the scope of the appended claims.

We claim:

1. A computer program for labeling a container of prescribed medicine for a pharmacy establishing a supplier relationship with long term care facilities, the computer program tangibly stored on a non-transitory computer-readable medium, containing instructions for causing a computer to:
    assemble a patient database for patients in the long term care facilities, comprising
        downloading photographs of patients of the long term care facilities;
        implementing the patient database for the long team care facilities, the patient database comprising:
            a database record for each patient that includes a patient's name, photograph, the patient's long term care facility, prescriptions, prescription numbers, and a prescription tracking code;
    generate labels for prescriptions for the long term care facilities by accessing the patient database and retrieving data for the labels;
    receive information from the long term care facilities with respect to accuracy of the labels; and
    modify the patient database based on the received information.

2. The computer program of claim 1 further comprising instructions for causing a computer to send a set of photographs and matching patient names from the patient database to a long term care facility for those patients for verification.

3. The computer program of claim 2 further comprising instructions for causing a computer to send patient-related information in association with the set of photographs for verification.

4. The computer program of claim 2 wherein the send comprises sending a grid comprising the set of patient photographs and the matching patient names.

5. The computer program of claim 1 wherein the long term care facility is for the elderly.

6. The computer program of claim 1 wherein the receive comprises receiving patient names in connection with photographs from the long term care facilities.

7. A method of delivering containers comprising
generating a label using the computer program of claim 1;
associating the label with a container of prescribed medication; and
delivering the container of prescribed medication to a patient of a long term care facility.

8. The computer program of claim 1 wherein database record further comprises a patient identifier.

9. The computer program of claim 8 further comprising instructions for causing a computer to receive the prescription tracking code, wherein the prescription tracking code is a combination of a national drug code and patient identifier.

10. The computer program of claim 9 further comprising instructions for causing a computer to encode for machine readability the prescription tracking code.

11. The computer program of claim 8 wherein the patient identifier is a code generated by the long term care facilities.

12. The computer program of claim 8 further comprising instructions for causing a computer to combine a national drug code and patient identifier into the prescription tracking code.

13. The computer program of claim 12 further comprising instructions for causing a computer to further combine the prescription tracking code with one or more items selected from prescription preparation date, pharmacy identifier, care facility identifier, pharmacist identifier.

14. The computer program of claim 13 wherein each of the pharmacy identifier, care facility identifier, and pharmacist identifier is a code.

15. A computer program for labeling a container of prescribed medicine for a pharmacy establishing a supplier relationship with long term care facilities, the computer program tangibly stored on a non-transitory computer-readable medium, containing instructions for causing a computer to:
receiving perform, organizing, and storing at least name, photograph, and prescription of a patient of a long term care facility into a patient record and implementing a patient database with, the patient database comprising a database record for each patient that includes a patient's name, photograph, the patient's long term care facility, prescriptions, prescription numbers, and a prescription tracking code;
generate labels for prescriptions for the long term care facility by accessing a patient record and retrieving data for the labels;
receive information from the long term care facilities with respect to the accuracy of the labels; and
modify a patient record based on the information from the long term care facility regarding accuracy of the labels.

16. The computer program of claim 15 further comprising instructions for causing a computer to send a set of photographs and matching patient names from the patient database to a long term care facility for those patients for verification.

17. A computer implemented method for labeling a container of prescribed medicine for a pharmacy establishing a supplier relationship with long term care facilities, comprising:
assembling by a computer system, a patient database for patients in the long term care facilities, comprising (a) downloading photographs of patients of the long term care facilities; and (b) implementing the patient database for the long term care facilities, the patient database comprising a database record for each patient that includes a patient's name, photograph, the patient's long term care facility, prescriptions, prescription numbers, and a prescription tracking code;
generating by the computer system, labels for prescriptions for the long term care facilities by accessing the patient database and retrieving data for the labels;
receiving by the computer system, information from the long term care facilities with respect to accuracy of the labels; and
modify by the computer system, the patient database based on the received information.

18. The method of claim 17 wherein a database record further comprising a patient identifier.

19. The method of claim 18 further receiving by the computer system the prescription tracking code, wherein the prescription tracking code is a combination of a national drug code and patient identifier.

20. A computer system for labeling a container of prescribed medicine for a pharmacy establishing a supplier relationship with long term care facilities, comprising:
a patient database comprising a database record for each patient that includes a patient's name, photograph, the patient's long term care facility, prescriptions, prescription numbers, and a prescription tracking code;
a computer configured by instructions to:
assemble the patient database for patients in the long term care facilities, comprising (a) downloading photographs of patients of the long term care facilities; and (b) implementing the patient database for the long term care facilities;
generate labels for prescriptions for the long term care facilities by accessing the patient database and retrieving data for the labels;
receive information from the long term care facilities with respect to accuracy of the labels; and
modify the patient database based on the received information.

* * * * *

UNITED STATES PATENT AND TRADEMARK OFFICE
CERTIFICATE OF CORRECTION

PATENT NO.         : 8,131,394 B2                                   Page 1 of 1
APPLICATION NO.    : 11/835638
DATED              : March 6, 2012
INVENTOR(S)        : Ruben et al.

It is certified that error appears in the above-identified patent and that said Letters Patent is hereby corrected as shown below:

Column 4:
Line 47 claim 1, change "team" to -- term --.

Column 5:
Line 43 claim 15, change "receiving perform," to -- perform receiving, --.
Line 46 claim 15, change "with, the" to -- with the --.

Signed and Sealed this
Seventeenth Day of April, 2012

David J. Kappos
*Director of the United States Patent and Trademark Office*